United States Patent [19]

Elmqvist et al.

[11] Patent Number: 4,541,430
[45] Date of Patent: Sep. 17, 1985

[54] METHOD AND A HEART PACEMAKER FOR TERMINATING A TACHYCARDIA

[75] Inventors: Hakan Elmqvist, Bromma; Hans Strandberg, Sundbyberg, both of Sweden

[73] Assignee: Siemens Aktiengesellschaft, Berlin & Munich, Fed. Rep. of Germany

[21] Appl. No.: 546,457

[22] Filed: Oct. 28, 1983

[30] Foreign Application Priority Data

Nov. 2, 1982 [DE] Fed. Rep. of Germany ....... 3240430

[51] Int. Cl.⁴ ............................................. A61N 1/36
[52] U.S. Cl. ............................................. 128/419 PG
[58] Field of Search ............. 128/419 D, 419 PG, 705

[56] References Cited

U.S. PATENT DOCUMENTS 3,942,534 3/1976 Allen et al. .
4,222,385 9/1980 Backhouse .................. 128/419 PG
4,280,502 7/1981 Baker, Jr. et al. .
4,312,356 1/1982 Sowton et al. .
4,388,928 6/1983 Ekwall et al. ................. 128/419 PG 4,406,287 9/1983 Nappholz et al. .......... 128/419 PG

FOREIGN PATENT DOCUMENTS

2076655 12/1981 United Kingdom .

Primary Examiner—William E. Kamm
Attorney, Agent, or Firm—Hill, Van Santen, Steadman & Simpson

[57] ABSTRACT

A routine is provided in order to be able to terminate a detected tachycardia quickly and reliably, the routine generating a sequence of n stimulation pulses, checking the heart reaction and, under given conditions, changing the sequence until the sequence terminates the tachycardia. The effective sequences are stored in a plurality of registers and are employed in a prescribable order for controlling the stimulation pulses. In addition to the traditional electronics, a heart pacemaker for the implementation of this method contains a tachycardia detector, a memory having N registers for the sequences to be stored, as well as a control logic for the selection of the registers and/or for changing the register values.

18 Claims, 5 Drawing Figures

FIG 4

METHOD AND A HEART PACEMAKER FOR TERMINATING A TACHYCARDIA

BACKGROUND OF THE INVENTION

The invention relates to a method of operating a heart pacemaker for the termination of a tachycardia and also relates to a heart pacemaker for the implementation of this method.

The unnaturally elevated frequency of the heartbeat, for example when the heart executes more than 180 beats per minute, is referred to as a tachycardia. It is known that this rapid heart rhythm can be stopped by means of electric stimulation pulses when it has been caused by retrograde transconduction. The prerequisite, however, is that a stimulation pulse must be emitted to the heart within a critical time interval after a tachycardia heartbeat, a so-called time window. This time window can lie immediately after the refractory time following a heartbeat or can lie only immediately before a next heartbeat. It is further known from investigations that individual stimulation pulses do not always suffice to effectively terminate a tachycardia but that sequences consisting of a plurality of stimulation pulses can be required. It can be necessary for terminating a tachycardia that the intervals between the individual pulses of a sequence differ in length. Investigations have further shown that the effective sequences can depend on the physical position of the patient, on physical activities, drugs and the like. Further, the required sequence can vary greatly from patient to patient. It is not possible for the above reasons to identify a fixed sequence for even one patient that can always reliably terminate a tachycardia.

A series of methods or, respectively, heart pacemakers are already known which are concerned with how the proper point in time for the stimulation can be found. Thus, U.S. Pat. 3,942,534 discloses a method wherein the time interval between the end of the refractory time and the next following tachycardia heartbeat is scanned in equidistant steps. Since the time window can be very small, the steps must be selected very small so that a sweep of the possible time interval can last very long under certain conditions.

A heart pacemaker is known from U.S. Pat. 4,312,356 wherein the reaction of the heart to a stimulation pulse is detected and employed for the control of the interval up to the next stimulation pulse such that the change of the interval is respectively carried out in a direction of the interval size effective for the termination of a tachycardia.

Known, finally, from U.S. Pat. 4,280,502 is a heart pacemaker wherein, upon occurrence of a tachycardia, the interval between the end of the refractory time and the next tachycardia heartbeat is likewise scanned until an effective stimulation for the termination of the tachycardia has been found. In addition, the refractory time can be identified in advance in a similar manner. The advantage of this known method and heart pacemaker is that the value, once found, can be stored in a register and, upon occurrence of a repeated tachycardia, can be employed as a first experimental value for the termination thereof.

SUMMARY OF THE INVENTION

The object of the present invention is to improve the method for the termination of a tachycardia such that an occurring tachycardia can be terminated as quickly as possible for any patient at all and independently of the external conditions to which a patient is respectively subject. Further, a heart pacemaker is to be created with which the said method can be implemented in a simple and reliable manner.

This object is achieved by means of the method steps recited in claim 1. The invention defined by these method steps proceeds from the perception that a sequence of n stimulation pulsesis necessary for the termination of a tachycardia, whereby each of the stimulation pulses of this sequence must be emitted to the heart at a specific point in time. As a limiting case of the sequence, it should also be understood that n can assume the value one, i.e. that the sequence actually consists only of single pulses.

As investigations have shown, the effective sequences form regions in an n-dimensional space constructed from the possible times of the individual intervals of the sequences. Given n=1, i.e. single pulses, these regions consist of the known time windows.

The inventive method now provides that the n-dimensional space is scanned in one of the known manners upon the first appearance of a tachycardia until an effective sequence for the termination of the tachycardia has been found and that said effective sequence is stored in a register of a memory. Upon renewed appearance of a tachycardia, these stored values are first interrogated and emitted to the heart as a first sequence. Should this sequence prove ineffective, the routine for finding an effective sequence is started again and the value thus identified is input into a further register of the memory. Over the course of time, all registers of the memory are filled in this manner with sequences that were effective at least once for the termination of a tachycardia.

The method also provides the possibility that selected sequences are stored in the registers from the beginning and that stimulation is first carried out with these sequences.

For every tachycardia appearing anew, the stored sequences are tried first in order to see whether one of these stimulations can already successfully terminate the tachycardia. The invention thereby proceeds from the perception that it is all the easier to terminate a tachycardia, the fewer attempts thereto are undertaken, i.e. the faster the effective sequence is found. The probability that one of these stored values is already effective is greatly enhanced due to the multitude of sequences stored in the registers, all of which can have arisen under various external conditions. Should all register values prove ineffective, then a new routine for finding an effective sequence is started and this value is input into one of the provided registers. The originally existing value is thereby cancelled.

It is provided in an advantageous further development of the invention that the existing register values are exploited in a manner such that the effective sequence is found even faster insofar as possible. Various alternatives are possible to that end. Thus, for example, the sequences can be stored and/or exploited in the order in which they appeared.

One parameter for the appearance of differing sequences can, for example, also be the length of the tachycardia interval. The found sequences can therefore be classified according to the tachycardia intervals (RR intervals) belonging to them and can subsequently be used on the basis of how close the interval of a renewed tachycardia approaches the stored tachycardia intervals. A further or even additional possibility consists in allocating a quality number to each register, said quality number depending on how often a sequence residing in the corresponding register was effective or ineffective.

It is provided in an advantageous further development of the method for the reduction of the memory requirements that only one interval of each sequence is stored in the registers and repeatedly employed. Sequences having equidistant intervals thus derive. Further, the time for scanning the n-dimensional space for the detection of an effective sequence can be considerably reduced when this scanning is restricted to sequences having specific intervals. Given equal intervals, the time is thus reduced to a value corresponding to the $n^{th}$ root of the time otherwise required.

A heart pacemaker for the implementation of the method disclosed according to the present invention consists of a traditional heart pacemaker electronics as standard, for example, for an inhibited or synchronized heart pacemaker which need not be discussed in detail within the framework of the invention and also consists of a tachycardia detector that receives signals from the heart pacemaker electronics when a heart signal exists or, for example, a stimulation pulse has been detected. The heart pacemaker, further, contains a memory with N registers into which at least N respective sequences of n stimulation pulses can be input and whose register values serve for setting the delivery point in time of the stimulation pulses generated by the known heart pacemaker electronics. A control logic clocked by the tachycardia detector thereby selects a respective register and/or takes care of a change of the stored values in a respective register.

Further advantages of the invention derive from the subject matter of the dependent claims.

The invention is explained and described in greater detail below with reference to four Figures on the accompanying drawing sheets; and other objects, features and advantages will be apparent from this detailed disclosure and from the appended claims.

DETAILED DESCRIPTION

Figure 1:
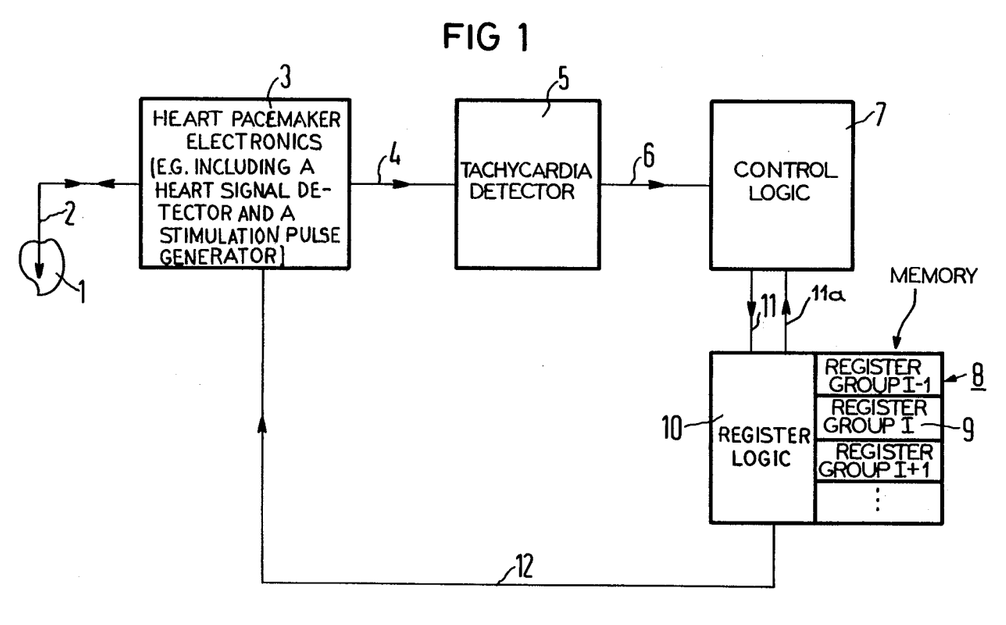
FIG. 1 illustrates the fundamental structure of an inventive heart pacemaker, by means of a block diagram.

In FIG. 1, 1 schematically indicates a heart into which an electrode 2 is introduced. By way of example, it is of no significance to the present invention whether one and the same electrode is employed for delivering stimulation pulses and for sensing heart potentials or whether a bipolar electrode or even a plurality of single electrodes are employed for this purpose. It is likewise of no consequence for this invention where the stimulation and where the sensing in the heart occurs. The electrode 2 is connected to traditional heart pacemaker electronics that is indicated by the block 3 and that contains, for example, a heart signal detector, a stimulation pulse generator, as well as a measuring means for determining various time intervals. The heart pacemaker electronics generates an output signal on a line 4 when the electrode 2 has registerd a heart activity or a stimulation pulse. The output signal proceeds to a tachycardia detector 5 which, for example, identifies the frequency of the received signals and, depending on the magnitude of said frequency, determines whether a tachycardia exists or not. Over a line 6, the output signal of said tachycardia detector starts or stops a control logic 7 by which a memory 8 having a plurality of register means is controlled. The selection of the respective register means 9 is determined by the control logic 7 and whether the data stored in the register means is to be altered is also determined thereby. The memory 8 also contains a register logic 10 for the readout or, respectively, change of the individual register values. The output signal of the memory 8 is fed back over a line 11a to the control logic 7. Further, said output signal is forwarded as a control signal over the line 12 to the traditional heart pacemaker electronics 3 for the control of the stimulation times as a function of the heart events. The term "line" is used to include individual conductors, groups of conductors, as well as data bus lines.

Figure 2A:
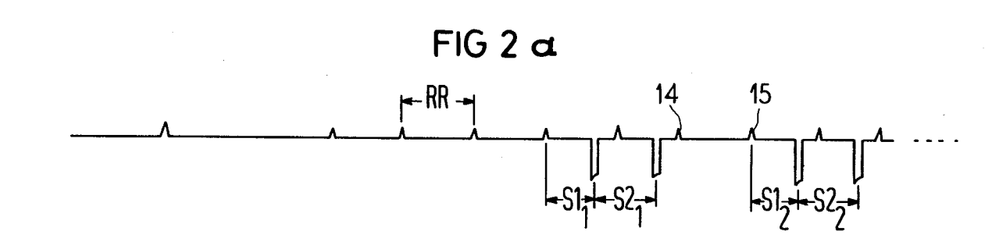
FIGS. 2a and 2b show two plots as a function of time of different signals that can, for example, be registered by means of an ECG device.
Figure 2B:
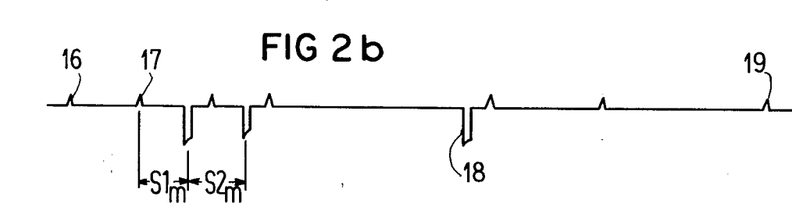

The chronological course of the signals registered by the electrode 2 is described in greater detail with reference to FIG. 2 by way of example and is used to explain the method for terminating a tachycardia in greater detail. In FIG. 2a natural heart activities are illustrated as positive spikes and stimulation pulses are illustrated as negative spikes on an arbitrary chronological scale. The first two, natural heart beats thus lie at such a great distance from one another that a normal heart frequency exists. The chronological spacing of the following positive spikes is so small that the heart is situated in a tachycardia condition. The interval between two tachycardia heartbeats is reference RR in FIG. 2a.

It is indicated by way of example in FIG. 2a that a first sequence of stimulation pulses is emitted to the heart after the fourth tachycardia heartbeat (after the fifth positive spike in FIG. 2a) in order to terminate the tachycardia. The first stimulation pulse of such first sequence occurs at a time interval $S1_1$ after the latest (fourth) tachycardia heartbeat. The second stimulation pulse of this sequence lies a time span $S2_1$ after said first stimulation pulse. Sequences having two stimulation pulses are illustrated here by way of example. However, it should be expressly pointed out that individual stimulation pulses can already successfully terminate a tachycardia under certain conditions or that it can also be necessary to employ sequences having more than two stimulation pulses.

Said first sequence is first followed by a check interval in which no further stimulation is undertaken. In the present example, this interval consists, for example, of the two heartbeat signals 14 and 15 registered subsequent to the last stimulation pulse of the first sequence. When, as in the present example, tachycardia continues to exist, then stimulation is undertaken again, this time, though, with a different sequence $S1_2S2_2$.

This procedure is continued until an effective sequence for the termination of the tachycardia has been found. An effective sequence is illustrated in FIG. 2b, following further heartbeat signals 16 and 17 which may represent continued tachycardia in spite of prior stimulation pulse sequences such as indicated in FIG. 2a. In FIG. 2b, the effective sequence $S1_m$, $S2_m$ may include a time interval $S2_m$ which is of shorter duration than previous time intervals such as $S2_1$ and $S2_2$. No natural heartbeat occurs at all in the following check interval, so that the traditional heart pacemaker electronics emits a single stimulation pulse 18 to the heart after a predetermined time. The timing of the last spike 19 of this chronological illustration shows that the heart has returned to a natural heartbeat sequence.

Figure 3:
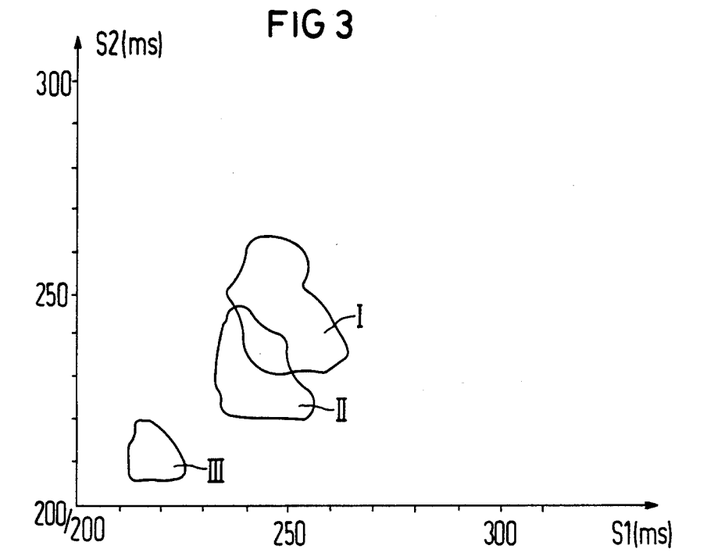
FIG. 3 illustrates regions of effective sequences by means of a two-dimensional diagram.

FIG. 3 shows effective sequences for the termination of a tachycardia by way of example. The different regions I, II, III are here based on different external conditions for the patient. Thus, region I can apply to a resting, lying patient; region II can apply to a seated patient; and region III, for example, can apply to a patient under stress. The regions can also partially overlap, but do not do so for all regions and not for all patients. In the diagram according to FIG. 3, the time interval S1 is entered on the abscissa and the time interval S2 is entered on the ordinate, both in milliseconds (ms). Let it again be pointed out here that the time S1 is measured from the preceding tachycardia heartbeat (such as 17, FIG. 2b) but that the time S2 is measured from the preceding stimulation pulse of a sequence.

It is self-understood that the times can also be defined in some other manner.

In the illustration according to FIG. 3, further, the coordinate intersection has been respectively selected at 200 ms, i.e. only a small time segment of the overall time range is illustrated. For the sake of simplicity, only one sequence having two stimulation pulses has again been employed for illustration (n=2). A three-dimensional structure would derive in a corresponding manner given three stimulation pulses for the sequences (n=3).

As can be derived from FIG. 3, a tachycardia can last rather long under certain conditions before an effective sequence has been found by means of scanning the entire possible region. The need to repeat this scanning upon every reoccurrence of tachycardia is therefore a situation that places considerable stress on the patient. Even the storage of an individual effective stimulation value and purposeful searching in its immediate proximity first provide no significant alleviation. When, for example, this stored effective value lies in the region III according to FIG. 3 and the patient is in a different physical condition upon renewed appearance of a tachycardia, then searching in the proximity of region III only prolongs the unsuccessful time before discovery of a new effective sequence.

As a result of the inventive method, by contrast, a multitude of effective sequences are made available from the beginning and these can all be tried out in a short time. The probability that one of these stored sequences will be effective again is thereby rather high. When, moreover, an ordering (or weighting) of the individual sequences is also undertaken, i.e. these are provided, for example, with a quality number, then this probability can even be considerably increased. In FIG. 3, for example, it can be derived from the overlap of the two regions I and II that an effective sequence in this overlap area is already effective for two different situations to which that patient is exposed, so that such sequences can terminate a tachycardia with greater probability.

Figure 4:
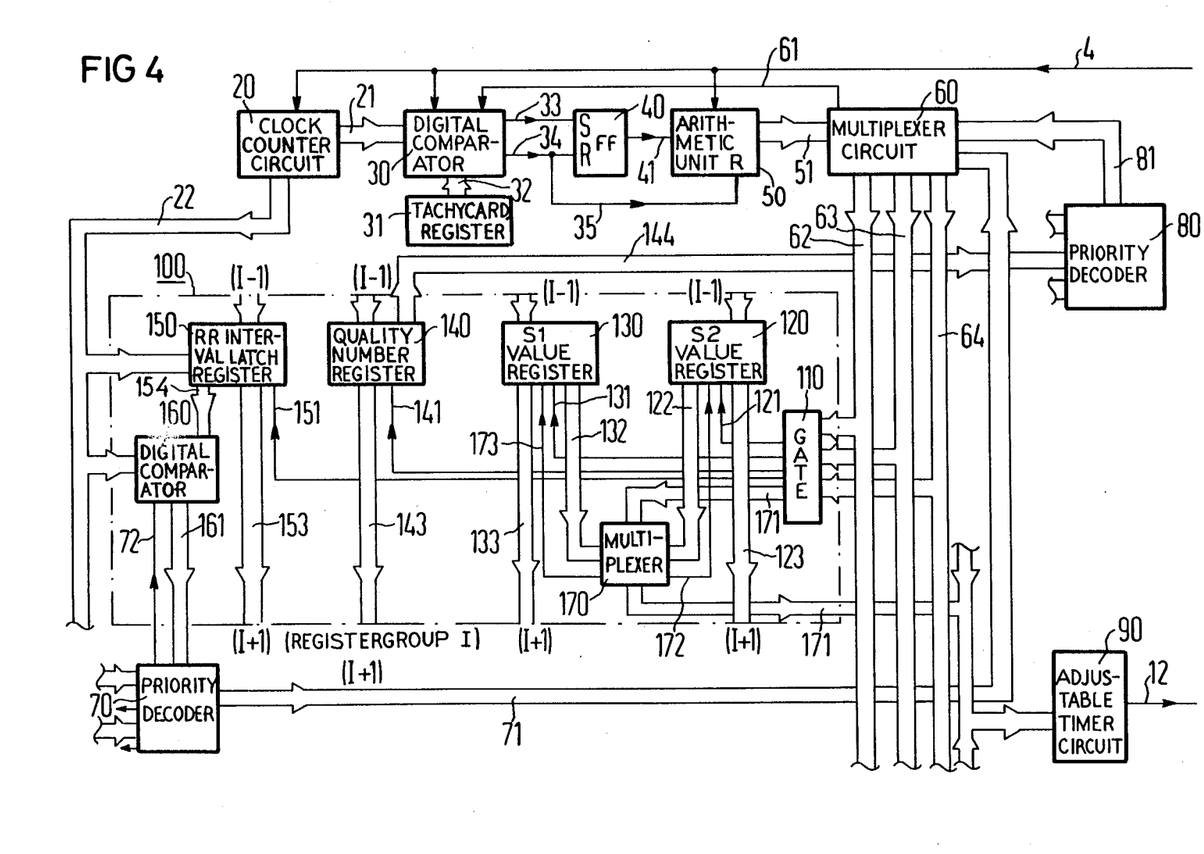
FIG. 4 illustrates a specific embodiment of the inventive heart pacemaker with the exception of the traditional heart pacemaker electronics, by means of a further block diagram.

The essential, new parts of the heart pacemaker are described and explained in a further block diagram in FIG. 4 for purposes of further explanation of the invention, particularly of a heart pacemaker for the implementation of the described method. The traditional heart pacemaker electronics 3 according to FIG. 1 has not been shown in FIG. 4 for the sake of clarity. The interface practically proceeds through the lines 4 and 12 respectively according to FIG. 1.

The signals received from the heart pacemaker electronics over the line 4 are forwarded as reset signals to a clock counter 20, as keying pulses to a digital comparator 30 and as clock signal to a counter of arithmetic unit 50. The readings of the counter 20 are continuously transmitted over a data line 21 to the digital comparator 30 to which, moreover, a selectable comparison value is supplied from a tachycardia register over a further line 32. The output signals of the digital comparator proceed over lines 33 or, respectively, 34 to the set or, respectively, reset input of a memory element 40 (e.g. a bistable flip-flop) whose output signal is forwarded to the counter 50 as an enable signal over a line 41. The output signal of the digital comparator 30 is also forwarded over the line 35 to the reset input of the arithmetic unit 50.

The arithmetic unit 50 is connected via a data line 51 to a mulitplexer 60. An enable signal can be emitted from the latter to the digital comparator 30 over a line 61.

Further, various data lines 62, 63 and 64 proceed from the multiplexer 60 to the individual register groups or register means. Only a single register group 100 is shown in FIG. 4 for the sake of clarity. The structure of the further register groups is identical to this. The number N of register groups is arbitrary.

The signals of the multiplexer 60 first proceed to a logical gate circuit 110 and from there via lines 121, 131, 141 and 151 to four registers 120, 130, 140, and 150 as well as via line 171 to a multiplexer 170. In the present exemplary embodiment, each register group or register means contains four registers, of which forward/backward counters are employed for three. The fourth register is a so-called latch register 150. The count values, i.e. the register values, residing in the counters 120 and 130 can be forwarded over respective data lines 122 and 132 to the multiplexer 170. The registers of the register group 100 are connected to corresponding registers of neighboring register groups (such as group I +1 shown in FIG. 1) over data lines such as 123, 133, 143 and 153. Further, each register group 100 contains a controllable digital comparator 160 to which, just like to the latch register 150, the tally data of the counter 20 are supplied over a data line 22. In addition, the circuit contains two priority decoders 70 and 80 respectively to which signals from the digital comparator 160 and, respectively, the forward/backward counter 140 are supplied over lines 161 and 144, respectively. The output signals of the decoders 70 and 80 respectively are forwarded over lines 71 and 81 respectively to the multiplexer 60 as additional control signals.

A control signal also proceeds to the digital comparator 160 from the priority decoder 70 over a line 72. As also indicated, it is not only signals of the illustrated register group 100 but also the corresponding signals of the remaining register groups that are forwarded to the two decoders. Finally, the circuit contains an adjustable timer 90 to which the output signals of the multiplexer 170 are supplied over a data line 171.

The manner of functioning of the circuit is as follows:

The counter 20 is clocked by an oscillator (not illustrated here) and is reset by each detected heart signal. When the following digital comparator 30 has received an enable signal from the multiplexer 60 over the line 61, the count value existing immediately prior to the resetting of the counter 20 is compared to the value read in from the tachycardia register 131. When a tachycardia condition is thereby detected, then the memory element 40 is set and the counter of arithmetic unit 50 is enabled. Otherwise, the memory element 40 and the counter 50 are reset.

The counter of arithmetic unit 50 is clocked by the detected heart signals and controls the multiplexer 60 with its count value. It is assumed in the present exemplary embodiment that the data line 62 serves for selection of the register group (such as I−, 1 I, I+1, etc., FIG. 1) to be activated and the data line 63 serves for the control of the individual registers within the register group. The data line 64, for example, serves for the control of the multiplexer 170.

It is further assumed for the present exemplary embodiment that the sequence of the stimulation pulses exhibits two different time intervals S1 and S2. That includes the possibility of constructing a sequence with a plurality of time intervals, for example in the form S1, S1, S2 or S1, S2, S1. It is now assumed that the forward-/backward counter 120 serves for storing the time interval S2 and that the forward/backward counter 130 serves for storing the time interval S1.

When the register group 100 has been selected by the multiplexer 60, then the multiplexer 170 successively through-connects the register values of the forward-/backward counters 120 and 130, respectively, to the adjustable timer 90 which thus emits a control signal via line 12 to the rest of the heart pacemaker electronics for setting the stimulation times in relationship to the heart events. A check is again subsequently carried out in the digital comparator 30 as to whether the tachycardia condition is still met or not. When tachycardia continues to exist, then the multiplexer 60 can either select the next register group (e.g. register group I+1 adjacent register group 100) and the procedure is repeated or the original register group (e.g. register group I, designated by reference numeral 100) can be retained and the counter contents, i.e. the register values of the counters 120 and 130 respectively, are changed. How and in which direction this change occurs can be controlled by the multiplexer 170 and line 172 and/or line 173. The register contents can be changed in this manner until an effective sequence for the termination of a tachycardia exists. The possibility of setting, particularly externally setting from outside the pacemaker, the register comprised of components 120 and 130 to prescribable, particularly programable values is not explicitly illustrated here.

The corresponding RR interval of the tachycardia (see FIG. 2a) is additionally stored in the latch register 150. The output signal of that register is supplied over a data line 754 to the digital comparator 760. Said RR interval can be compared in the digital comparator 160 to the current RR interval. This comparison is correspondingly executed in all register groups. The signals of the digital comparator 160 of each group are forwarded to a shared priority decoder 70 in which that stored RR interval which comes closest to the current interval is determined. The digital comparator 70 can be controlled for this purpose such that the comparison is first roughly executed and is subsequently executed progressively more exactly step-by-step. It can be achieved with the assistance of this comparison and of the priority decoder 70— whose signal is forwarded via line 71 to the multiplexer 60 as a control signal— that the sequences stored in the individual register groups are exploited in an order dependent on the respective RR interval.

The circuit also contains a forward/backward counter 140 for storing a quality number. The control and the clocking of this memory occur over the line 141. The stored quality number is supplied via the data line 144 to a further priority decoder 80 to which the quality numbers of all other register groups are correspondingly supplied. The output signal of this decoder 80 proceeds over a further data line 81 to the multiplexer 60, likewise as an additional control signal. It is additionally possible in this matter to define the order in which the various register groups are exploited by means of these quality numbers. When a sequence represented as stored register values in a register group is effective for the termination of a tachycardia, then the count content of the forward/backward counter 140 is increased as a result, i.e. the quality number is raised. When, on the other hand, the employed sequence is ineffective, then the quality number is reduced in an analogous manner.

For reasons of surveyability, a series of clock signals as well as some gate circuits to the various registers and, under given conditions, delay elements potentially expedient for the time-suited function sequence are not explicitly illustrated in the circuit shown in FIG. 4.

The circuit specifies an advantageous exemplary embodiment of a heart pacemaker. It is possible, however to omit parts such as, for example, the RR register latch register 150 or the register(quality register 140) for the quality number without departing from the framework of the invention.

A simple possibility for exploiting the register groups and for changing the register values can, for example, also be provided in that each new, effective sequence is rolled into the first of the N register groups and the existing register values are respectively shifted into the next register group. The sequence stored in the $N^{th}$ register group is thereby cancelled.

Other combinations are also conceivable. Thus, for example it is also possible to realize at least parts of the illustrated circuit with one or more microprocessors.

It will be apparent that many modifications and variations may be made without departing from the scope of the teachings and concepts of the present invention.

We claim as our invention:

1. A heart pacemaker for supplying sequences of stimulation pulses for effecting termination of a sensed tachycardia, said pacemaker comprising at least a signal detector, a controllable stimulation pulse generator for generating stimulation pulses with a controllable time interval, and a tachycardia detector, and further comprising a memory with a plurality of register means constructed for storing respective register values controlling generation of respective sequences of n stimulation pulses, said register means during pacemaker operation serving to store register values corresponding to respective sequences that are effective for the termination of a tachycardia and thereafter to supply the stored, register values during a subsequent tachycardia to control the generator to again supply the corresponding sequence, and control logic means coupled with said tachycardia detector for activation in response to a tachycardia and controlling selection of the respective register means to selectively effect the supply of the respective stored register values for the corresponding control of said generator.

2. A heart pacemaker according to claim 1, characterized in that the memory is coupled to the control logic means so that the output of the memory is fed back to the control logic means.

3. A heart pacemaker according to claim 1, characterized in that the appertaining tachycardia interval (RR) is storable in the respective register means in addition to respective register values.

4. A heart pacemaker according to claim 1, characterized in that a quality number can be desposited in every register means, the selection of the register means by the control logic means being based on the apertaining quality number stored, by said register means.

5. A heart pacemaker according to claim 1, characterized in that the control logic means comprises at least an arithmetic element clocked as a function of the heart activity, and a multiplexer by which the individual registers means are selected and by which the register values can be set in said register means.

6. A heart pacemaker according to claim 1, characterized in that each register means comprises at least two forward/backward counters of which the one serves to store the time interval for an initial stimulation pulse of a sequence and the other serves to store the time interval for a further stimulation pulse of the sequence.

7. A heart pacemaker according to claim 1, with at least part of the tachycardia detector being formed by a microprocessor.

8. A heart pacemaker according to claim 1, with at least part of the control logic means being formed by a microprocessor.

9. A heart pacemaker according to claim 1, with at least part of the memory being formed by a microprocessor.

10. A method for operating a heart pacemaker for the termination of a tachycardia, comprising the following method steps:
 (a) detecting a tachycardia,
 (b) initiating a routine for terminating the tachycardia comprised of:
  (1) generating at least one first sequence having a number n of stimulation pulses within an n-dimensional space defined by the possible times S1 . . . Sn of said stimulation pulses, where n is an integer,
  (2) checking the heart reaction in response to the at least one first sequence,
  (3) changing at least one characteristic of the sequence comprised of time interval and number n of the pulses of the sequence when the at least one first sequence fails to effect termination of the tachycardia,
  (4) generating successive further sequences with the at least one characteristic successively changed to scan the n-dimensional space until an effective sequence for the termination of the tachycardia is generated, and
  (5) storing the at least one characteristic of the effective sequence as a register value in one of N registers of a memory,
 (c) storing successive register values representing the at least one characteristic of other effective sequences in other of said N registers of said memory, and assigning to the stored register values priority criteria related to an order of future use of the stored register values,
 (d) with a plurality of said N registers containing stored register values and having assigned priority criteria as a result of step (c), detecting a further tachycardia, and in response thereto successively generating previously effective sequences under the control of the respective stored register values and in an order based on the assigned priority criteria until one of the previously effective sequences is again effective to terminate the tachycardia, and
 (e) when all such previously effective sequences are ineffective, generating successive new sequences for the termination of the tachycardia, and checking the heart reaction to each successive new sequence.

11. A method for operating a heart pacemaker for the termination of a tachycardia, comprising the following method steps:
 (a) detecting a tachycardia,
 (b) initiating a routine for terminating the tachycardia comprised of:
  (1) generating at least one first sequence having a number n of stimulation pulses within an n-dimensional space defined by the possible times S1 . . . Sn of said stimulation pulses, where n is a number equal to or greater than one,
  (2) checking the heart reaction in response to the at least one first sequence,
  (3) changing at least one characteristic of the sequence comprised of time interval and number n of the pulses of the sequence when the at least one first sequence fails to effect termination of the tachycardia,
  (4) generating successive further sequences with the at least one characteristic successively changed to scan the n-dimensional space until an effective sequence for the termination of the tachycardia is generated, and
  (5) storing the at least one characteristic of the effective sequence as a register value in one of N registers of a memory,
 (c) storing successive register values representing the at least one characteristic of other effective sequences in other of said N registers of said memory,
 (d) with a plurality of said N registers containing stored register values as a result of step (c), detecting a further tachycardia, and in response thereto successively generating previously effective sequences under the control of the respective stored register values in a prescribable order until one of the previously effective sequences is again effective to terminate the tachycardia, and
 (e) when all such previuosly effective sequences are ineffective, generating successive new sequences for the termination of the tachycardia, and checking the heart reaction to each successive new sequence, and
 (f) when all of said N registers have register values therein pursuant to the storing operation of step (c), replacing a stored register value in one of said N registers with a new register value representing a new sequence generated pursuant to step (e) which is effective.

12. A method according to claim 11, wherein step (d) is carried out by generating the previously effective sequences in the order in which they were most recently effective.

13. A method according to claim 11, wherein in addition to the storing of the at least one characteristic of the effective sequences in said N registers of said memory, the appertaining tachycardia intervals are also stored in the respective registers, the generating of the previously effective sequences, in respone to a renewed appearance of a tachycardia with a new tachycardia interval, being in an order based on how close the new tachycardia interval is to the respective stored tachycardia intervals.

14. A method according to claim 11, wherein a relative quality number is assigned to each register, said quality number being raised every time the corresponding sequence is effective in the termination of a tachycardia and being lowered when the sequence is ineffective, the generating of the previously effective sequences being in an order based on the magnitudes of the quality numbers stored in the respective appertaining registers.

15. A method according to claim 11, with the number n of the stimulation pulses being greater than one and with equal intervals between the individual pulses of each sequence, the stored register value in each register representing a respective interval between the individual pulses and the number of stimulation pulses in the sequence, the generation of the previously effective sequences being controlled to have a number of stimulation pulses and an interval therebetween according to the respective stored register values.

16. A method according to claim 11, wherein the generating operation of step (b)(4) generates further sequences having a plurality of stimulation pulses and where each further time interval of each sequence is a function of a first time interval of the sequence.

17. A method according to claim 16, wherein each further time interval of each sequence is a linear function of the first order of the first time interval of the sequence.

18. A method according to claim 17 where the further time interval of each sequence is equal in duration to the first time interval of the sequence.

* * * * *